(12) United States Patent
Cho et al.

(10) Patent No.: US 6,350,411 B1
(45) Date of Patent: *Feb. 26, 2002

(54) MICROPOROUS HOLLOW FIBER BLOOD OXYGENATOR

(75) Inventors: Kwantai Cho, Charlotte, NC (US); Clifton James Delozier, Fort Mill, SC (US); Robert English Johnston, Pineville, NC (US)

(73) Assignee: Celgard Inc., Charlotte, NC (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/046,341

(22) Filed: Mar. 23, 1998

(51) Int. Cl.[7] ............... A61M 1/14; A61M 1/36; A61M 1/34; A61M 37/00
(52) U.S. Cl. ............... 422/45; 422/48; 422/44; 604/4.01; 604/6.14; 261/DIG. 28
(58) Field of Search ............... 422/44–45, 48; 261/DIG. 28, 2, 5, 75, 100–3, 105–6; 210/645–47, 650, 252, 257, 321.6, 321.72–321.79, 348, 511; 604/4.01, 6.13, 6.14

(56) References Cited

U.S. PATENT DOCUMENTS

| 4,239,729 A | * | 12/1980 | Hasegawa et al. | |
| 4,530,809 A |   | 7/1985  | Shindo et al. | 264/210.7 |
| 4,541,981 A | * | 9/1985  | Lowery et al. | 264/209.1 |
| 4,564,488 A |   | 1/1986  | Gerlach et al. | 264/41 |
| 4,859,535 A |   | 8/1989  | Shinomura et al. | 428/398 |
| 4,906,375 A | * | 3/1990  | Heilmann | 210/500.23 |
| 5,057,641 A | * | 10/1991 | Valus et al. | 585/818 |
| 5,152,964 A |   | 10/1992 | Leonard | 422/48 |
| 5,489,382 A | * | 2/1996  | Tatebe et al. | 210/321.89 |
| 5,489,413 A |   | 2/1996  | Carson et al. | 422/46 |
| 5,547,756 A |   | 8/1996  | Kamo et al. | 428/394 |
| 5,695,545 A |   | 12/1997 | Cho et al. | 95/46 |
| 5,695,717 A | * | 12/1997 | Polaschegg et al. | 422/48 |
| 6,001,306 A | * | 12/1999 | McFall et al. | |

FOREIGN PATENT DOCUMENTS

| EP | 507 722 A1 | 3/1992 |
| EP | 0713709 A2 | 11/1995 |

OTHER PUBLICATIONS

Tamari, Yehuda, et al., Artificial Organs vol. 15, No. 1. p. 15–22, (1991).
Montoya, J.P., et al. ASAIO Journal, vol. 38 p. M399–M405 (1992).

* cited by examiner

Primary Examiner—Angela D. Sykes
Assistant Examiner—Patricia Bianco
(74) Attorney, Agent, or Firm—Robert H. Hammer, III

(57) ABSTRACT

The present invention is to a process for blood oxygenation using a microporous fiber membrane. The use of the hollow fiber allows improvements in plasma break through results. The oxygenator includes a housing and microporous membrane cartridge. The cartridge comprises a microporous hollow fiber membrane having a wall thickness greater than 30 microns and having a bubble point of ≧150 psig.

6 Claims, 1 Drawing Sheet

MICROPOROUS HOLLOW FIBER BLOOD OXYGENATOR

FIELD OF THE INVENTION

The present invention is directed to the use of a thick walled microporous hollow fiber membrane in a blood oxygenator.

BACKGROUND OF THE INVENTION

Blood oygenators, as used herein, refers to the medical device that is used to maintain oxygen levels in the blood during surgery, for example heart by-pass surgery. A popular blood oxygenator uses microporous hollow fibers as the interface between the oxygen and the blood. See, for example, U.S. Pat. Nos. 5,489,413; 5,152,964; European Application Publication 507,722; 713,709.

In the use of these devices, 'plasma leakage' or 'plasma breakthrough' may be a problem. See: Tamari, Yehuda, et. al., "The Effect of High Pressure on Microporous Membrane Oxygenator Failure", *Artificial Organs,* Vol. 15, No. 1, pg. 15–22, (1991); and Montoya, J.P., et al., "Plasma Leakage Through Microporous Membranes," *ASAIO Journal,* Vol. 38 pg. M399–405(1992). Plasma leakage is the movement of liquid through the micropores of the membrane from the blood side to the gas side of the device.

Accordingly, there is a need to improve the plasma breakthrough of microporous hollow fiber membranes.

The microporous hollow fiber membrane used herein are disclosed in U.S. Pat. No. 5,695,545. Other known hollow fibers are disclosed in U.S. Pat. Nos. 4,564,488; 4,530,809; 4,859,535; & 5,547,756.

SUMMARY OF THE INVENTION

The present invention is to a process for blood oxygenation using a microporous fiber membrane. The use of the hollow fiber allows improvements in plasma break through results. The oxygenator includes a housing and microporous membrane cartridge. The cartridge comprises a microporous hollow fiber membrane having a wall thickness greater than 30 microns and a bubble point of $\geq$150 psig.

DESCRIPTION OF THE DRAWINGS

For the purpose of illustrating the invention, there shown in the drawings a form which is presently preferred; it being understood, however, that this invention is not limited to the precise arrangement and instrumentalitites shown.

DETAILED DESCRIPTION OF THE INVENTION

Figure 1:
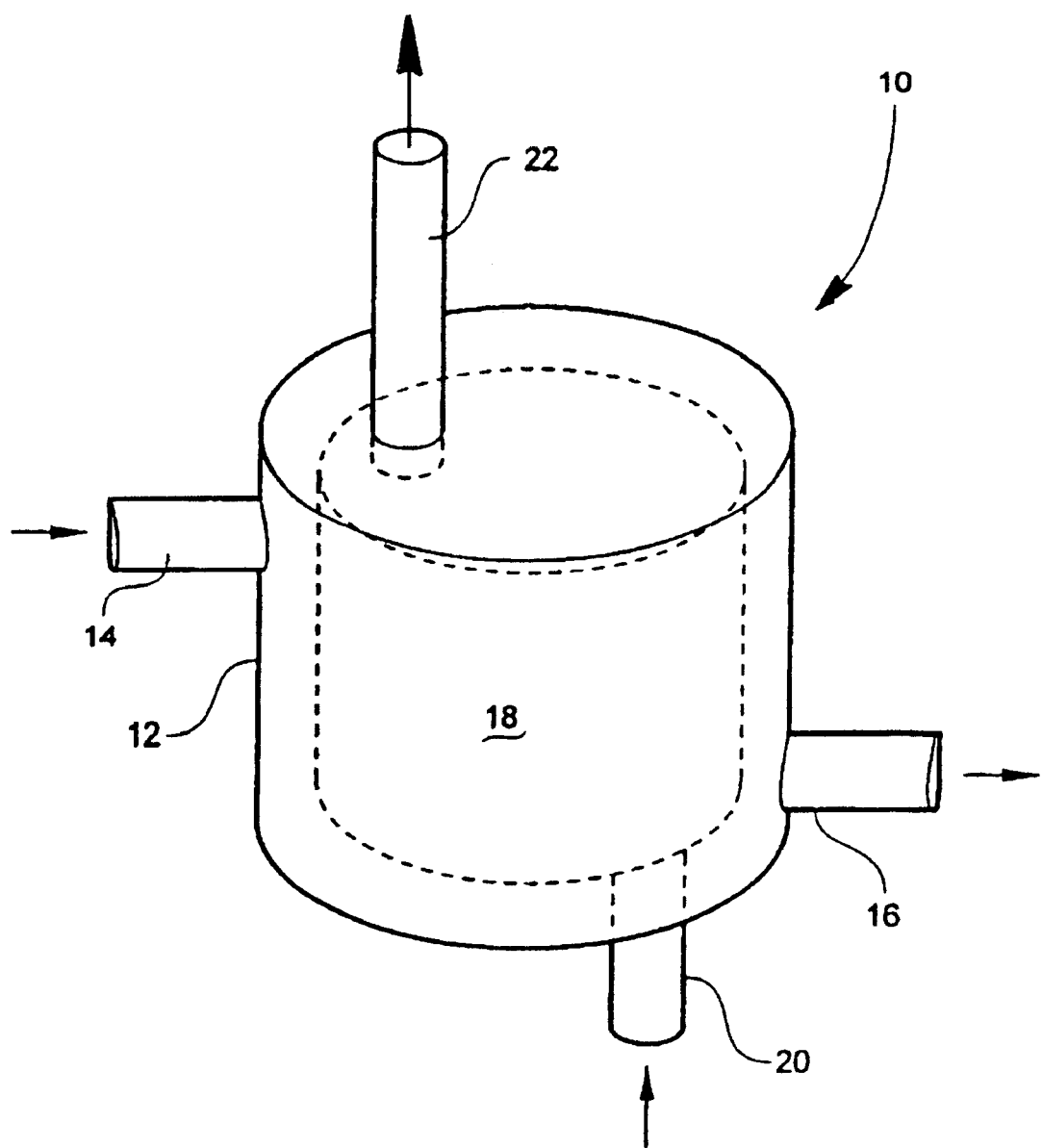
FIG. 1 is a schematic illustration of a blood oxygenator.

Referring to FIG. 1, there is shown a blood oxygenator 10. Oxygenator 10 may be any hollow fiber oxygenator and is not limited to any particular design. Oxygenator 10 comprises, in general, a housing 12 and hollow fiber cartridge 18. Housing 12 has a blood inlet 14 and a blood outlet 16. Cartridge 18 is located within housing 12. Cartridge 18 is any hollow fiber device. Cartridge 18 has an oxygen inlet 20 and an oxygen outlet 22. The hollow fiber used in the oxygenator is discussed in greater detail below.

Microporous hollow fibers preferably: are made of a polyolefin material having a wall thickness of greater than 30 micron (more preferably greater than 35 microns, and most preferably greater than or equal to ($\geq$) 50 microns); have a porosity of less than 80% (more preferably less than 60%, and most preferably about 40%); have a Gurley number of greater than 1 (more preferably greater than 10, and most preferably about 50); have a bubble point of greater than or equal to 150 psig (more preferably greater than 200 psig, and most preferably greater than 250 psig); and have a shrinkage, under no load, of less than 5% at 90° C. for 60 minutes (preferably about 2% or less). The hollow fiber disclosed in U.S. Pat. No. 5,695,545 is incorporated herein by reference.

Polyolefin refers a class group of thermoplastic polymers derived from simple olefins. Exemplary polyolefins include, but are not limited to, polyethylene, polypropylene, polymethylpentene, copolymers of polyethylene, copolymers of polypropylene, copolymers of polymethylpentene, and combinations thereof. Preferably, the polyolefin is polypropylene which will be discussed hereinafter.

The polypropylene is preferably crystalline and has a crystallization temperature of greater than or equal to 125° C. To obtain this crystalline polypropylene, it is preferably nucleated. Nucleated or having a nucleating agent refers to the promotion of crystal nucleation which is often initiated by a material added to the polymer. Preferred nucleating agents may be selected from the group of sodium benzoate or sorbital acetate or combinations thereof. The preferred nucleating agent is sodium benzoate. Preferably, about 2400 ppm of nucleating agent is added to the polymer. The nucleated material is beneficial from at least two stand points. First, the better crystal uniformity provides greater heat stability. Second, the better crystal uniformity reduces the polymer's tendency to "creep" or close or shrink the pore size.

The polypropylene has a melt flow index (ASTM D1238-85) of greater than 0.1 gram per 10 minutes, preferably greater than 1 gram per 10 minutes and most preferably in a range of 0.1 to 20 grams per 10 minutes.

With regard to polyolefin resin selection, one should consider the additive package or stabilizer that customarily is present in all commercially available resins because some of these stabilizers can cause pore closure or pore shrinkage and/or skin formation on the fiber surface. For example, a stabilizer consisting of: 0.05% of BHT (butylated hydroxytoluene or 2,6-di-t-butyl-4-methyl phenol); 0.12% (Irganox 1010 from Ciba Geigy Corp.) tetrakis[methylene (3,5-di-butyl-r-hydroxyhydrocinnamate)] methane; and 32 ppm calcium sterate, caused complete pore blockage and a skin formed on the fiber surface. It is believed that this stabilizer leached from the polymer to block the pores and to skin the fiber surface. On the other hand, a stabilizer consisting of: 600 ppm hinder phenolic (Ethyl 330 from Ethyl Corp.) and 1000 ppm phosphite (Orgafox from Ciba Geigy Corp.), had no effect on the pores or fiber surface. Based upon the foregoing, the following stabilizer selection criteria is proposed: a stabilizer that will not migrate is preferred, such stabilizer may have high molecular weights and/or side chains consisting of long hydrocarbons (e.g., nonpolar, chemically more compatible with polyolefins); and a lower amount of stabilizer (so that there is less material to migrate).

The following is a preferred procedure by which a microporous hollow fiber according to the instant invention is made. The resin is polypropylene (Fina PP3362 from Fina Co.). The extrusion temperature was 210° C., the extrusion speed was 100 m/min, and spinning tension was 21 grams. Rapid quenching was not necessary in view of the nucleating agent (about 2400 ppm sodium benzoate). After fiber spinning, the fiber was drawn. The spun fiber had a 332 micron OD and a 55 micron wall thickness. It was annealed at 150° C. Then, it was subjected to a 10% cold draw, a 50% hot draw (at 142° C.), and thereafter to a 20% relax (at 142° C.). The resulting fiber had the following properties: 325 micron OD; 215 micron ID; 55 micron wall thickness; 250 sec/m$^2$ —Gurley number; 250 psi—bubble point; 1.2%—shrinkage; 1.02—shape ratio; 460 g—tensile strength, and 220%—elongation at break.

All measured values set forth herein are measured according to conventional industry standards (e.g. appropriate ASTM procedures), the following values are discussed in greater detail.

Gurley

"Gurley refers to a measure of the resistance to air flow through the wall of the microporous hollow fiber. The resistance to airflow, as measured by a Gurley densometer, is the time in seconds required to pass 10 cc of air through one square inch of product at a constant pressure of 12.2 inches of H$_2$O. The measure is reported in "sec/in$^2$ " and is normalized in the one square inch value.

Bubble Point

"Bubble point" is a measure for determining the large pore diameter and the general pore diameter of the hollow fiber. About one foot of hollow fiber is tested using nitrogen pressure gas in a methanol bath. The initial pressure is 15 psig and is increased at about 5–10 psig per second. The measurement is calculated when 15 streamers of bubbles appear. The bubble point, herein, is reported in psig and correlates to pore size in microns by: (micron)=6.56/(psig in methanol bath).

Porosity

"Porosity" is a measure of the interior pore volume and the apparent pore diameter distribution of the hollow fiber. Porosity is measured in accordance with the procedures set forth in ASTM D-2873-89.

In a plasma breakthrough test, based upon the work of Tamari et al, 1991, Ibid. (Three microporous hollow fibers were tested for plasma break through. See Table 1. Example A thin walled, large pore membrane, Example B is a thin walled, small pore membrane. Example C is a thick walled small pore membrane. Example C has a superior plasma breakthrough (50% better than Example B and 400% better than Example A).

TABLE 1

| SAMPLE | WALL THICKNESS Micron (μm) | Pore size (μm) | Pore size psi* | Breakthrough (hr) |
|---|---|---|---|---|
| A[1] | 30 | 0.05 | 100 | 30 |
| B[1] | 30 | 0.03 | 200 | 80 |
| C | 50 | 0.03 | 200 | 120 |

*bubble point
[1]prior art

The present invention may be embodied on other forms without departing from the spirit and essential attributes thereof and, accordingly, reference should be made to the appended claims, rather to the foregoing specification, as indicating the scope of the invention.

What is claimed is:

1. In a process for blood oxygenation comprising the steps of:

providing a blood oxygenator having a housing having a blood inlet and a blood outlet and a microporous membrane cartridge located within said housing, said cartridge comprising a microporous hydrophobic hollow fiber membrane having a wall thickness greater than 30 microns, having a pore size ≦0.03 micron, and a plasma breakthrough of >80 hours, and said hollow fiber's lumen being in communication with an oxygen source.

2. The process according to claim 1 wherein said fiber membrane having a bubble point ≧150 psig.

3. In the process of claim 1 wherein said membrane is polypropylene.

4. A blood oxygenator comprising:

a housing having a blood inlet and a blood outlet, and a microporous membrane cartridge located within said housing, said cartridge comprising a microporous hydrophobic hollow fiber membrane having a wall thickness greater than 30 micron, having a pore size ≦0.03 micron, and a plasma breakthrough of >80 hours, and said hollow fiber's lumen being in communication with an oxygen source.

5. The oxygenator of claim 4 wherein said membrane is polypropylene.

6. The blood oxygenator according to claim 4 wherein said fiber membrane having a bubble point ≧150 psig.

* * * * *